United States Patent
Chang

(10) Patent No.: US 7,232,444 B2
(45) Date of Patent: Jun. 19, 2007

(54) MICRODERMABRASION CANISTER RACK SYSTEM

(76) Inventor: Mei Yin Chang, 1971 W Holt Ave., Pomona, CA (US) 91768

( * ) Notice: Subject to any disclaimer, the term of this patent is extended or adjusted under 35 U.S.C. 154(b) by 292 days.

(21) Appl. No.: 10/602,836

(22) Filed: Jun. 24, 2003

(65) Prior Publication Data
US 2004/0267285 A1 Dec. 30, 2004

(51) Int. Cl.
*A61B 17/50* (2006.01)

(52) U.S. Cl. ............... 606/131; 451/39; 211/85.18
(58) Field of Classification Search ........... 211/85.18; 348/310; 606/131; 29/438; 451/39
See application file for complete search history.

*Primary Examiner*—Corrine McDermott
*Assistant Examiner*—Christopher Prone
(74) *Attorney, Agent, or Firm*—Clement Cheng

(57) ABSTRACT

A canister rack system for a microdermabrasion machine has a base with bores. The base has conduits for crystal passage through the canister rack. The canisters are mountable upon the canister rack and include supply and storage canisters. The supply canister has a feeding conduit for the exit of crystal from the supply canister and the storage canister has a return conduit and a filtered conduit. The canister rack bores are formed at the base so that the conduits from the storage canister and supply canister meet with their respective conduits to form an airtight seal. A Horizontal locking pin protrudes from each canister and locks into a pair of horizontal slots formed in the canister rack. A vertical locking pin protrudes from the base of the canister rack and locks into a slot formed in each canister. A latch attaches each canister to the canister rack.

8 Claims, 2 Drawing Sheets

MICRODERMABRASION CANISTER RACK SYSTEM

DISCUSSION OF RELATED ART

Plastic Surgeons for the past ten years have used a procedure called Micro-Dermabrasion to treat various types of skin blemishes. In the procedure, a machine is used which contains Aluminum Oxide crystals, Sodium Chloride, or Baking Soda particles flowing in a continuous air stream. Particles exit through an exit tube, and brush against a patients skin in order to smoothen their upper skin layer. Immediately after brushing against a patient's skin, the particles are sucked into a vacuum tube and re-circulated through the machine.

The Microdermabrasion process uses a stream of fine crystals to polish and smooth skin. Crystals are commonly stored in a first chamber to be pumped against a person's skin at high velocity, and then collected to a second chamber. The cleaning of the chambers and exchange of chambers has been cumbersome.

Microdermabrasion machines typically contain two canisters, a storage canister and a waste canister, between which the small particles flow. After each individual use, surgeons must refill the storage canister with new particles and dispose of the particles in the waste canister. Currently, the commonly used Threaded Bore Canister Design complicates this process. The threaded attachment portions are often cross-threaded by continual unscrewing. Also every time that the canisters are unscrewed, fine abrasive dust is released. When unscrewing waste canisters, there is the added danger of releasing abraded skin particles into the work environment.

Inventor Metcalf in U.S. Pat. No. 6,238,275 details a microdermabrasion machine which uses a threaded bore mechanism on the top plate of the canister. Inventor Ignon in U.S. Pat. No. 6,527,783, Inventor Di Fiore in U.S. Pat. No. 6,527,783 and Inventor Owen in U.S. Pat. No. 6,562,050 all show a threaded bore mechanism similar to that described above.

Other prior art does not focus on the method of attachment for the canisters.

DETAILED DESCRIPTION OF THE PREFERRED EMBODIMENT

Figure 1:
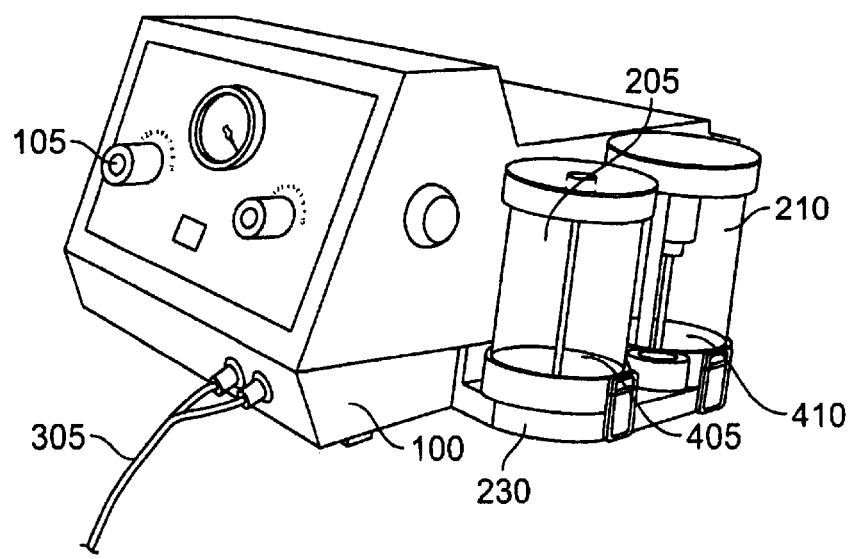
FIG. 1 is a front view of the machine.
Figure 2:
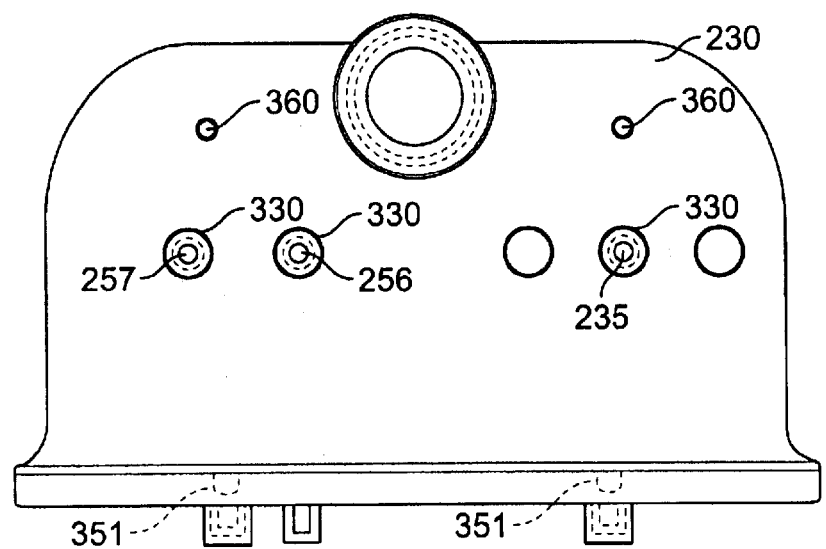
FIG. 2 is a top view of the rack.
Figure 3:
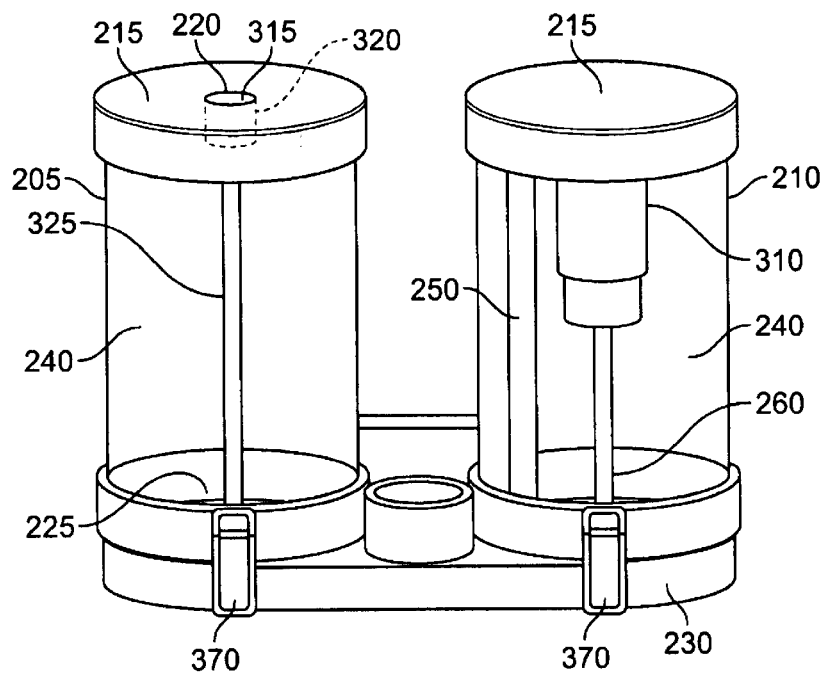
FIG. 3 is a front view of the rack filled with canisters.
Figure 4:
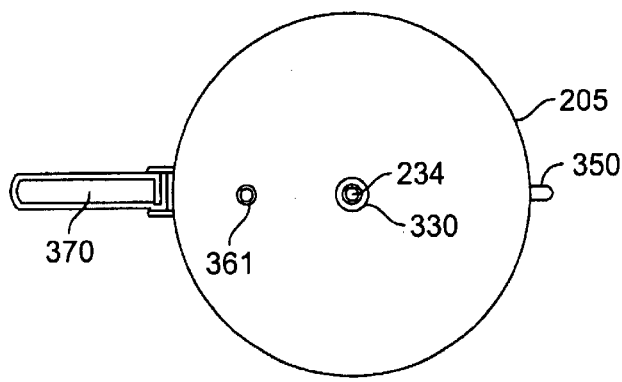
FIG. 4 is a bottom view of a supply canister.
Figure 5:
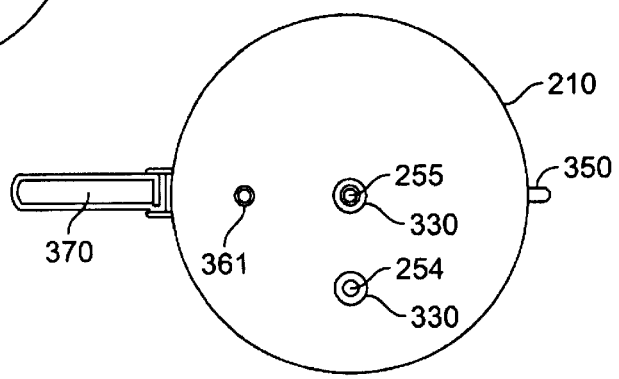
FIG. 5 is a bottom view of a storage canister.

The present embodiment includes a pair of canisters, a first canister for supplying crystal called a supply canister 205 and a second canister for storing crystal, the storage canister 210. The crystal begins in the first canister 205 and is connected by conduits 305 to the second canister 210. A vacuum 105 applied to the second canister 210 produces an air pressure imbalance that moves airflow. The airflow flows from the first canister 205 to the second canister 210. The crystals 405 stored in the first canister travel in the airflow and through a network of conduits to the second canister 210. The crystals 405 are retained in the storage canister 210 also called the second canister 210 by means of a filter 310 that prevents crystals from passing through.

Both canisters have tops 215 that can be opened for cleaning and replacement of crystal. The supply canister 205, initially full of crystals 405, has an Air inlet 315 on its top 215. The air inlet 315 further includes a filter 320 preventing dust and ambient suspended particles from entering the supply canister 205. The air filter 320 may be formed of a sponge-like material and disposed within a bore 220 located on the top of the supply canister top 215.

The supply canister 205 further includes a feeding conduit 325 formed of a metal tube intruding within the canister from the canister bottom 225 and rising vertically to a level above the pile of initial crystal supply. The feeding conduit 325 beginning with a metal tube open at the top continues through the bottom of the supply canister 205 and through the base of the canister rack 230 into the microdermabrasion machine 100 for the use on a patient.

The canister rack 230 holds the pair of canisters. The canister rack can be made of machined aluminum. The interface of the metal rack to the supply canister is a simple one. An O-ring 330 disposed around the bottom portion of the feeding conduit 325 maintains an airtight seal between the bore 220 in the bottom of the canister and the bore in the metal canister rack 235. The O-ring 330 holds itself in place by interference fit. Made of rubber, the O ring 330 fits snugly into a circumferential indentation surrounding the interface of the canister rack bore 235 and the supply canister bore 220 so that the crystal experiences uninterrupted travel through both portions of the feeding conduit 325, namely the upper portion which is the metal tube and the lower portion which is a bore through the canister rack 230.

The canister rack 230 also holds a storage canister 210 receiving used Crystal 410 from the microdermabrasion machine 100. The used Crystal 410 having been in contact with a person's skin may contain skin particles that should most likely be trapped within the storage canister 210.

The storage canister 210 has a pair of tubes protruding into the canister cavity 240. A first storage canister tube 250 extends vertically from a bore 255 in the bottom of the canister to an outlet above the level of a normal pile of crystal 405. The first storage canister tube 250 comprises a portion of the return conduit that returns used Crystal to the storage canister. The remainder of the return conduit is in the canister rack 230 and machine 100.

The second storage canister tube 260 also extends vertically from a bore 255 in the bottom of the canister to outlets above the normal pile of crystal but further includes a filter 310 preventing crystal from leaving the canister. The second storage canister tube forms the top portion of the vacuum conduit 105. The vacuum conduit connects to a pump.

The first and second storage canister tube connects to respective bores in the bottom of the canister. A pair of O-rings disposed around the bore extending into the base maintains an airtight seal between the bore in the bottom of the canister and the bore in the metal canister rack.

Both canisters have similar attachment means for attachment to the canister rack. A horizontal locking pin 350 on the inside face of each canister protrudes horizontally from the base of the canister and mates with a slot in the canister rack. A vertical locking pin 360 near the outside face on the canister rack protrudes vertically and mates with a slot in the bottom of the canister. The locking pin is a short protrusion. A pair of latches 370 formed on each outside face attaches each canister to the canister rack. The latch can be opened and closed by one hand. Preferably, the latch secures to a slot on the underside of the canister rack.

A machine operator begins with an empty pair of canisters. The operator opens the top of the supply of canister and fills the supply canister with crystals. The machine operator then aligns the supply canister so that the locking pin on the inside face of the canister rack aligns with the slot in the inside face of the canister rack. The machine operator then secures the latch of the inquiry canister now filled with crystals. As the operator secures the latch, the O-ring forms a seal that later allows continuous flow of crystals from the supply canister to the machine. The operator then secures the storage canister in a similar manner.

What is claimed is:

1. A canister rack system for a microdermabrasion machine comprising:
   a canister rack having a base with bores through the base forming conduits for crystal passage through the canister rack, to a microdermabrasion machine;
   a pair of canisters mountable upon the canister rack, including a supply canister and a storage canister, wherein the supply canister has a feeding conduit for the exit of crystal from the supply canister, wherein the storage canister has a return conduit and a filtered conduit;
   wherein the canister rack bores forming conduits are formed at the base which is the interface between the canister rack and pair of canisters, so that the conduits from the storage canister and supply canister meet with their respective conduits formed in the canister rack to form an airtight seal;
   a horizontal locking pin protruding from one of either the canister rack or each of the canisters, locking into a pair of horizontal slots formed in the other of the canister rack or each of the canisters;
   a vertical locking pin protruding from the base of the canister rack locking into a slot formed in each canister;
   a latch attaching each canister to the canister rack.

2. The canister rack system of claim 1, further comprising: o-rings disposed in the canister rack to seal the interface in the feeding conduit, return conduit, and filtered conduit.

3. The canister rack system of claim 1, wherein the horizontal locking pin protrudes from the canister rack and locks into a slot formed in the canister.

4. The canister rack system of claim 1, wherein the canister is cylindrical having a cylindrical main body threaded at an upper end to receive a screw on top and threaded at a lower end to receive a screw on bottom.

5. A canister rack system for a microdermabrasion machine comprising:
   a canister rack has a base with bores through the base forming conduits for crystal passage through the canister rack to a microdermabrasion machine;
   a supply canister and a storage canister mount on the canister rack, wherein the supply canister has a feeding conduit for crystal exit from the supply canister, wherein the storage canister has a return conduit and a filtered conduit;
   wherein the canister rack bores forming conduits are formed at the base which is the interface between the canister rack and pair of canisters, so that the conduits from the storage canister and supply canister meet with their respective conduits formed in the canister rack to form an airtight seal;
   a horizontal locking pin protruding from each canister locking into a pair of horizontal slots formed in the canister rack;
   a latch attaching each canister to the canister rack.

6. The canister rack system of claim 5, further comprising: o-rings disposed in the canister rack to seal the interface in the feeding conduit, return conduit, filtered conduit.

7. The canister rack system of claim 5, wherein the horizontal locking pin protrudes from the canister rack instead of the canister and locks into a slot formed in the canister instead of the canister rack.

8. The canister rack system of claim 5, wherein the canister is cylindrical having a cylindrical main body threaded at an upper end to receive a screw on top and threaded at a lower end to receive a screw on bottom.

\* \* \* \* \*